United States Patent
Drewes et al.

(12) 
(10) Patent No.: US 6,444,616 B1
(45) Date of Patent: Sep. 3, 2002

(54) SUBSTITUTED P-TRIFLUOROMETHYLPHENYLURACILS

(75) Inventors: Mark-Wilhelm Drewes; Roland Andree, both of Langenfeld (DE); Markus Dollinger, Kansas, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/628,381

(22) Filed: Aug. 1, 2000

Related U.S. Application Data

(62) Division of application No. 09/230,899, filed on Feb. 2, 1999, now Pat. No. 6,130,225.

(51) Int. Cl.$^7$ .................. C07D 239/54; A01N 43/54
(52) U.S. Cl. .................. 504/243; 544/310; 544/311; 544/312; 544/313; 544/314
(58) Field of Search ................... 544/310, 311, 544/312, 313, 314; 504/243

(56) References Cited

U.S. PATENT DOCUMENTS

| | | | |
|---|---|---|---|
| 5,116,404 A | 5/1992 | Ishii et al. | 71/92 |
| 5,681,794 A | 10/1997 | Andree et al. | 504/243 |
| 6,130,225 A | * 10/2000 | Drewes et al. | 514/274 |

FOREIGN PATENT DOCUMENTS

| | | |
|---|---|---|
| DE | 195 24 617 | 1/1997 |
| EP | 0 246 061 | 3/1992 |

OTHER PUBLICATIONS

Chem. Abstracts, vol. 119, No. 11, Abstract No. 117269m & JP 05 025142 Feb. 2, 1993.

J. Heterocycl. Chem. 9, p 513–522, (month unavailable) 1992.

* cited by examiner

*Primary Examiner*—John M. Ford
(74) *Attorney, Agent, or Firm*—Joseph C. Gil

(57) ABSTRACT

The invention relates to novel substituted p-trifluoromethylphenyluracils of the general formula (I)

(I)

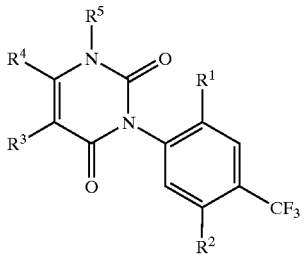

in which $R^1$, $R^2$, $R^3$, $R^4$ and $R^5$ are each as defined in the description, to a process for their preparation and to their use as herbicides.

4 Claims, No Drawings

SUBSTITUTED P-TRIFLUOROMETHYLPHENYLURACILS

This application is a divisional application of U.S. application Ser. No. 09/230,899, filed on Feb. 2, 1999, now U.S. Pat. No. 6,130,225.

The invention relates to novel substituted p-trifluoromethylphenyluracils, to a process for their preparation and to their use as herbicides.

It is known that certain substituted p-trifluoromethylphenyluracils, such as, for example, the compound 3-(3-chloro-4-trifluoromethyl-phenyl)-6-(2,6-difluoro-phenyl)-[1H,3H]-pyrimidine-2,4-dione, have pesticidal properties, i.e. they are active against certain animal pests, in particular against insects and mites (cf. JP 05025142—cited in Chem. Abstracts 119:117269). However, nothing has yet been disclosed about a herbicidal activity of these compounds.

This invention, accordingly, provides the novel substituted p-trifluoromethylphenyluracils of the general formula (I)

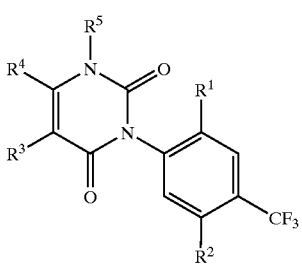

in which
$R^1$ represents hydrogen, cyano or halogen,
$R^2$ represents the grouping $A^1$—$A^2$—$A^3$ in which
$A^1$ represents a single bond, represents O, S, —SO—, —SO$_2$—, —CO— or the grouping —N—$A^4$— in which $A^4$ represents hydrogen, hydroxyl, alkyl, alkenyl, alkinyl, alkoxy, aryl, alkylsulphonyl or arylsulphonyl,
$A^1$ furthermore represents alkanediyl, alkenediyl, azaalkenediyl, alkinediyl, cycloalkanediyl, cycloalkenediyl or phenylene, each of which is optionally substituted by halogen,
$A^2$ represents a single bond, represents O, S, —SO—, —SO$_2$—, —CO— or the grouping —N—$A^4$13 in which $A^4$ represents hydrogen, hydroxyl, alkyl, alkoxy, aryl, alkylsulphonyl or arylsulphonyl,
$A^2$ furthermore represents alkanediyl, alkenediyl, azaalkenediyl, alkinediyl, cycloalkanediyl, cycloalkenediyl or phenylene, each of which is optionally substituted by halogen,
$A^3$ represents hydrogen, hydroxyl, mercapto, amino, cyano, isocyanato, thiocyanato, nitro, carboxyl, carbamoyl, thiocarbamoyl, sulpho, chorosulphonyl, halogen, represents alkyl, alkoxy, alkylthio, alkylsulphinyl, alkylsulphonyl, alkylamino, dialkylamino, alkoxycarbonyl or dialkoxy(thio) phosphoryl, each of which is optionally substituted by halogen or alkoxy, represents alkenyl, alkenyloxy, alkenylamino, alkylideneamino, alkenyloxycarbonyl, alkinyl, alkinyloxy, alkinylamino or alkinyloxycarbonyl, each of which is optionally substituted by halogen, represents cycloalkyl, cycloalkyloxy, cycloalkylalkyl, cycloalkylalkoxy, cycloalkylideneamino, cycloalkyloxycarbonyl or cycloalkylalkoxycarbonyl, each of which is optionally substituted by halogen, cyano, carboxyl, alkyl and/or alkoxy-carbonyl, or represents aryl, aryloxy, aralkyl, arylalkoxy, aryloxycarbonyl or arylalkoxycarbonyl, each of which is optionally substituted by nitro, cyano, carboxyl, halogen, alkyl, halogenoalkyl, alkyloxy, halogenoalkyloxy and/or alkoxy-carbonyl,
$A^3$ furthermore represents in each case optionally fully or partially hydrogenated pyrrolyl, pyrazolyl, imidazolyl, triazolyl, furyl, oxiranyl, oxetanyl, dioxolanyl, thienyl, oxazolyl, isoxazolyl, thiazolyl, isothiazolyl, oxadiazolyl, thiadiazolyl, pyridinyl, pyrimidinyl, triazinyl, pyrazolylalkyl, furylalkyl, thienylalkyl, oxazolylalkyl, isoxazolalkyl, thiazolalkyl, pyridinylalkyl, pyrimidinylalkyl, pyrazolylalkoxy, furylalkoxy, represents perhydropyranylalkoxy or pyridylalkoxy,
$R^3$ represents hydrogen, halogen or optionally halogen-substituted alkyl,
$R^4$ represents optionally halogen-substituted alkyl, and
$R^5$ represents hydrogen, amino or optionally hydroxyl-, cyano-, halogen- or alkoxy-substituted alkyl.

The novel substituted p-trifluoromethylphenyluracils of the general formula (I) are obtained when aminoalkenoic esters of the general formula (II)

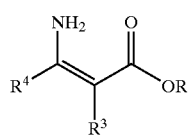

in which $R^3$ and $R^4$ are each as defined above and

R represents alkyl, aryl or arylalkyl are reacted with p-trifluoromethylphenyl isocyanates of the general formula (III)

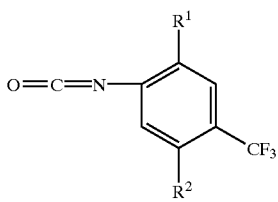

in which $R^1$ and $R^2$ are each as defined above or with p-trifluoromethylphenylurathanes (p-trifluoromethylphenylcarbamates) of the general formula (IV)

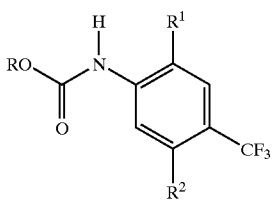

(IV)

in which
R$^1$ and R$^2$ are each as defined above and
R represents alkyl, aryl or arylalkyl,
if appropriate in the presence of a reaction auxiliary and if appropriate in the presence of a diluent,
and, if appropriate, further conversions within the scope of the above definitions of substituents are carried out by customary methods on the resulting compounds of the formula (I).

The compounds of the general formula (I) can be converted by customary methods into other compounds of the general formula (I) according to the above definitions of substituents, for example by customary electrophilic or nucleophilic substitution reactions (for example R$^2$: F→OH, SH, NH$_2$, OCH$_3$, SC$_2$H$_5$, NHC$_3$H$_7$, NHSO$_2$CH$_3$; R$^5$: HNH$_2$, CH$_3$)—cf. also the preparation examples.

The novel substituted p-trifluoromethylphenyluracils of the general formula (I) have strong herbicidal activity. Additionally, they are well tolerated by important crop plants, such as, for example, wheat, barley and maize.

In the definitions, the saturated or unsaturated hydrocarbon chains, such as alkyl, alkenyl or alkinyl—also in combination with heteroatom's, such as in alkoxy or alkylthio—are in each case straight-chain or branched.

Halogen generally represents fluorine, chlorine, bromine or iodine, preferably fluorine, chlorine or bromine, in particular fluorine or chlorine.

The invention preferably provides compounds of the formula (I) in which
R$^1$ represents hydrogen, cyano, fluorine, chlorine or bromine,
R$_2$ represents the grouping A$^1$—A$^2$—A$^3$ in which
A$^1$ represents a single bond, represents O, S, —SO—, —SO$_2$—, —CO— or the grouping —N—A$^4$— in which A$^4$ represents hydrogen, hydroxyl, C$_1$–C$_4$-alkyl, C$_1$–C$_4$-alkoxy, phenyl, C$_1$–C$_4$-alkylsulphonyl or phenylsulphonyl,
A$^1$ furthermore represents C$_1$–C$_6$-alkanediyl, C$_2$–C$_6$-alkenediyl, C$_2$–C$_6$-alkinediyl, C$_3$–C$_6$-cycloalkanediyl, C$_3$–C$_6$-cycloalkenediyl or phenylene, each of which is optionally substituted by fluorine or chlorine,
A$^2$ represents a single bond, represents O, S, —SO—, SO$_2$—, —CO— or the grouping —N—A$^4$— in which A$^4$ represents hydrogen, hydroxyl, C$_1$–C$_4$-alkyl, C$_1$–C$_4$-alkoxy, phenyl, C$_1$–C$_4$-alkylsulphonyl or phenylsulphonyl,
A$^2$ furthermore represents C$_1$–C$_6$-alkanediyl, C$_2$–C$_6$-alkenediyl, C$_2$–C$_6$-alkinediyl, C$_3$–C$_6$-cycloalkanediyl, C$_3$–C$_6$-cycloalkenediyl or phenylene, each of which is optionally substituted by fluorine or chlorine,
A$^3$ represents hydrogen, hydroxyl, mercapto, amino, cyano, isocyanato, thiocyanato, nitro, carboxyl, carbamoyl, thiocarbamoyl, sulpho, chlorosulphonyl, halogen, represents alkyl, alkoxy, alkylthio, alkylsulphinyl, alkylsulphonyl, alkylamino, dialkylamino, alkoxycarbonyl or dialkoxy(thio)phosphoryl having in each case 1 to 6 carbon atoms in the alkyl groups and being in each case optionally substituted by fluorine, chlorine, bromine or C$_1$–C$_4$-alkoxy, represents alkenyl, alkenyloxy, alkenylamino, alkylideneamino, alkenyloxycarbonyl, alkinyl, alkinyloxy, alkinylamino or alkinyloxycarbonyl having in each case 2 to 6 carbon atoms in the alkenyl, alkylidene or alkinyl groups and being in each case optionally substituted by fluorine, chlorine or bromine, represents cycloalkyl, cycloalkyloxy, cycloalkylalkyl, cycloalkylalkoxy, cycloalkylideneamino, cycloalkyloxycarbonyl or cycloalkylalkoxycarbonyl having in each case 3 to 6 carbon atoms in the cycloalkyl groups and optionally 1 to 4 carbon atoms in the alkyl groups and being in each case optionally substituted by fluorine, chlorine, bromine, cyano, carboxyl, C$_1$–C$_4$-alkyl and/or C$_1$–C$_4$-alkoxycarbonyl, or represents phenyl, phenyloxy, phenyl-C$_1$–C$_4$-alkyl, phenyl-C$_1$–C$_4$-alkoxy, phenyloxycarbonyl or phenyl-C$_1$–C$_4$-alkoxycarbonyl, each of which is optionally substituted by nitro, cyano, carboxyl, fluorine, chlorine, bromine, C$_1$–C$_4$-alkyl, C$_1$–C$_4$-halogenoalkyl, C$_1$–C$_4$-alkyloxy, C$_1$–C$_4$-halogenoalkyloxy and/or C$_1$–C$_4$-alkoxy-carbonyl, represents (in each case optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolyl-C$_1$–C$_4$-alkyl, furyl-C$_1$–C$_4$-alkyl, thienyl-C$_1$–C$_4$-alkyl, oxazolyl -C$_1$–C$_4$-alkyl, isoxazole-C$_1$–C$_4$-alkyl, thiazole-C$_1$–C$_4$-alkyl, pyridinyl-C$_1$–C$_4$-alkyl, pyrimidinyl-C$_1$–C$_4$-alkyl, pyrazolylmethoxy, furylmethoxy, represents perhydropyranylmethoxy or pyridylmethoxy,
R$^3$ represents hydrogen, fluorine, chlorine, bromine or optionally fluorine- and/or chlorine-substituted alkyl having 1 to 4 carbon atoms,
R$^4$ represents optionally fluorine- and/or chlorine-substituted alkyl having 1 to 4 carbon atoms, and
R$^5$ represents hydrogen, amino or optionally hydroxyl-, cyano-, fluorine-, chlorine- or C$_1$–C$_4$-alkoxy-substituted alkyl having 1 to 4 carbon atoms.

The invention in particular relates to compounds of the formula (I) in which
R$^1$ represents hydrogen, fluorine or chlorine,
R$^2$ represents the grouping A$^1$—A$^2$—A$^3$ in which
A$^1$ represents a single bond, represents O, S, —SO—, —SO$_2$—, —CO— or the grouping —N—A$^4$— in which A$^4$ represents hydrogen, hydroxyl, methyl, ethyl, n- or i-propyl, methoxy, ethoxy, n- or i-propoxy, methylsulphonyl or ethylsulphonyl,
A$^2$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl or propine-1,3-diyl,
A$^2$ represents a single bond, represents O, S, —SO—, —SO$_2$—, —CO— or the grouping —N—A$^4$— in which A$^4$ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, $A^2$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl or propine-1,3-diyl, $A^3$ represents hydrogen, hydroxyl, amino, cyano, nitro, carboxyl, carbamoyl, sulpho, fluorine, chlorine, bromine, represents methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl, dipropoxyphosphoryl or diisopropoxyphosphoryl, each of which is optionally substituted by fluorine, chlorine, methoxy or ethoxy, represents propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, each of which is optionally substituted by fluorine or chlorine, represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclo-propylmethoxy, cyclobutylmethoxy, cyclopentylmethoxy, cyclohexylmethoxy, cyclopentylideneamino, cyclohexylideneamino, cyclopentyloxycarbonyl, cyclohexyloxycarbonyl, cyclopentylmethoxycarbonyl or cyclohexylmethoxycarbonyl, each of which is optionally substituted by fluorine, chlorine, cyano, carboxyl, methyl, ethyl, n- or i-propyl, methoxycarbonyl or ethoxycarbonyl, or represents phenyl, phenyloxy, benzyl, phenylethyl, benzyloxy, phenyloxycarbonyl, benzyloxycarbonyl, each of which is optionally substituted by nitro, cyano, carboxyl, fluorine, chlorine, bromine, methyl, ethyl, n- or i-propyl, trifluoromethyl, methoxy, ethoxy, n- or i-propoxy, difluoromethoxy, trifluoromethoxy, methoxycarbonyl and/or ethoxycarbonyl, represents (in each case optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolyl, methyl, furylmethyl, thienylmethyl, oxazolylmethyl, isoxazolmethyl, thiazolemethyl, pyridinylmethyl, pyrimidinylmethyl, pyrazolylmethoxy, furylmethoxy or pyridylmethoxy, $R^3$ represents, hydrogen, fluorine, chlorine, bromine or in each case optionally fluorine- and/or chlorine-substituted methyl or ethyl, $R^4$ represents in each case fluorine- and/or chlorine-substituted methyl or ethyl, and $R^5$ represents hydrogen, amino or in each case optionally hydroxyl-, cyano-, fluorine-, chlorine-, methoxy- or ethoxy-substituted methyl or ethyl.

The general or preferred radical definitions given above apply both to the end products of the formula (I) and, correspondingly, to the starting materials or intermediates required in each case for the preparation. These radical definitions can be combined with each other as desired, that is to say combinations between the stated ranges of preferred compounds are also possible.

Examples of compounds of the formula (1) according to the invention are listed in the groups below.

Group I

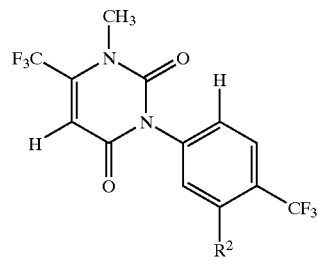

$R^2$ has, for example, the meanings given in the list below:

hydrogen, hydroxyl, mercapto, amino, fluorine, chlorine, bromine, methyl, ethyl, n- or i-propyl, n-, i-, s- or t-butyl, n-, i-, s- or t-pentyl, difluoromethyl, trifluoromethyl, chlorodifluoromethyl, fluorodichloromethyl, fluoroethyl, chloroethyl, chlorofluoroethyl, difluoroethyl, dichloroethyl, trifluoroethyl, trichloroethyl, chlorodifluoroethyl, tetrafluoroethyl, chlorotrifluoroethyl, pentafluoroethyl, fluoropropyl, chloropropyl, difluoropropyl, dichloropropyl, trifluoropropyl, cyanomethyl, cyanoethyl, cyanopropyl, cyanobutyl, carboxymethyl, carboxyethyl, carboxypropyl, carboxybutyl, methoxymethyl, ethoxymethyl, propoxymethyl, methoxyethyl, ethoxyethyl, propoxyethyl, methoxypropyl, ethoxypropyl, propoxypropyl, methoxycarbonylmethyl, ethoxycarbonylmethyl, propoxycarbonylmethyl, methoxycarbonylethyl, ethoxycarbonylethyl, propoxycarbonylethyl, methoxycarbonylpropyl, ethoxycarbonylpropyl, propoxycarbonylpropyl, 1-propen-3-yl (allyl), 3-methyl-1-propen-3-yl, 2-buten-4-yl (crotonyl), 1-propin-3-yl (propargyl), 3-methyl-1-propin-3-yl, 2-butin-4-yl, cyclopropyl, cyanocyclopropyl, carboxycyclopropyl, difluorocyclopropyl, dichlorocyclopropyl, methylcyclopropyl, methoxycarbonylcyclopropyl, ethoxycarbonylcyclopropyl, cyclobutyl, cyanocyclobutyl, carboxycyclobutyl, difluorocyclobutyl, trifluorocyclobutyl, tetrafluorocyclobutyl, chlorotrifluorocyclobutyl, methylcyclobutyl, cyclopentyl, cyanocyclopentyl, carboxycyclopentyl, fluorocyclopentyl, chlorocyclopentyl, difluorocyclopentyl, dichlorocyclopentyl, methylcyclopentyl, methoxycarbonylcyclopentyl, ethoxycarbonylcyclopentyl, cyclohexyl, cyanocyclohexyl, carboxycyclohexyl, fluorocyclohexyl, chlorocyclohexyl, difluorocyclohexyl, dichlorocyclohexyl, methylcyclohexyl, trifluoromethylcyclohexyl, methoxycarbonylcyclohexyl, ethoxycarbonylcyclohexyl, cyclopropylmethyl, difluorocyclopropylmethyl, dichlorocyclopropylmethyl, cyclobutylmethyl, cyclopentylmethyl, cyclohexylmethyl, cyanocyclohexylmethyl, carboxycyclohexylmethyl, fluorocyclohexylmethyl, chlorocyclohexylmethyl, methylcyclohexylmethyl, trifluoromethylcyclohexylmethyl, methoxy, ethoxy, n- or i-propoxy, n-, i-, s- or t-butoxy, n-, i-, s- or t-pentoxy, difluoromethoxy, trifluoromethoxy, chlorodifluoromethoxy, fluorodichloromethoxy, fluoroethoxy, chloroethoxy, chlorofluoroethoxy, difluoroethoxy, dichloroethoxy, trifluoroethoxy, trichloroethoxy, chlorodifluoroethoxy, tetrafluoroethoxy, chlorotrifluoroethoxy, pentafluoroethoxy, fluoropropoxy, chloropropoxy, difluoropropoxy, dichloropropoxy, trifluoropropoxy, cyanomethoxy, cyanoethoxy, cyanopropoxy, cyanobutoxy, carboxymethoxy, carboxyethoxy, carboxypropoxy, carboxybutoxy, methoxymethoxy, ethoxymethoxy, propoxymethoxy, methoxyethoxy, ethoxyethoxy, propoxyethoxy, methoxypropoxy, ethoxypropoxy, propoxypropoxy, methoxycarbonylmethoxy, ethoxycarbonylmethoxy, propoxycarbonylmethoxy, methoxycarbonylethoxy, ethoxycarbonylethoxy, propoxycarbonylethoxy, methoxycarbonylpropoxy, ethoxycarbonylpropoxy, propoxycarbonylpropoxy, 1-propen-3-yl-oxy (allyloxy), 3-methyl-1-propen-3-yl-oxy, 2-buten-4-yl-oxy (crotonyloxy), 1-propin-3-yl -oxy(propargyloxy), 3-methyl-1-propin-3-yl-oxy, 2-butin-4-yl-oxy, cyclopropyloxy, cyanocyclopropyloxy, carboxycyclopropyloxy, difluorocyclopropyloxy, dichlorocyclopropyloxy, methylcyclopropyloxy, methoxycarbonylcyclopropyloxy, ethoxycarbonylcyclopropyloxy, cyclobutyloxy, cyanocyclobutyloxy, carboxycyclobutyloxy, difluorocyclobutyloxy, trifluorocyclobutyloxy, tetrafluorocyclobutyloxy, chlorotrifluorocyclobutyloxy, methylcyclobutyloxy, cyclopentyloxy, cyanocyclopentyloxy, carboxycyclopentyloxy, fluorocyclopentyloxy, chlorocyclopentyloxy, difluorocyclopentyloxy, dichlorocyclopentyloxy, methylcyclopentyloxy, methoxycarbonylcyclopentyloxy, ethoxycarbonylcyclopentyloxy, cyclohexyloxy, cyanocyclohexyloxy, carboxycyclohexyloxy, fluorocyclohexyloxy, chlorocyclohexyloxy, difluorocyclohexyloxy, dichlorocyclohexyloxy, methylcyclohexyloxy, trifluoromethylcyclohexyloxy, methoxycarbonylcyclohexyloxy, ethoxycarbonylcyclohexyloxy, cyclopropylmethoxy, difluorocyclopropylmethoxy, dichlorocyclopropylmethoxy, cyclobutylmethoxy, cyclopentylmethoxy, cyclohexylmethoxy, cyanocyclohexylmethoxy, carboxycyclohexylmethoxy, fluorocyclohexylmethoxy, chlorocyclo-hexylmethoxy, methylcyclohexylmethoxy, trifluoromethylcyclohexylmethoxy, methylthio, ethylthio, n- or i-propylthio, n-, i-, s- or t-butylthio, n-, i-, s- or t-pentylthio, difluoromethylthio, trifluoromethylthio, chlorodifluoromethylthio, fluorodichloromethylthio, fluoroethylthio, chloroethylthio, chlorofluoroethylthio, difluoroethylthio, dichloroethylthio, trifluoroethylthio, trichloroethylthio, chlorodifluoroethylthio, tetrafluoroethylthio, chlorotrifluoroethylthio, pentafluoroethylthio, fluoropropylthio, chloropropylthio, difluoropropylthio, dichloropropylthio, trifluoropropylthio, cyanomethylthio, cyanoethylthio, cyanopropylthio, cyanobutylthio, carboxymethylthio, carboxyethylthio, carboxypropylthio, carboxybutylthio, methoxycarbonylmethylthio, ethoxycarbonylmethylthio, propoxycarbonylmethylthio, methoxycarbonylethylthio, ethoxycarbonylethylthio, propoxycarbonylethylthio, methoxycarbonylpropylthio, ethoxycarbonylpropylthio, propoxycarbonylpropylthio, 1-propen-3-yl-thio (allylthio), 3-methyl-1-propen-3-yl-thio, 2-buten-4-yl-thio, 1-propin-3-yl-thio (propargylthio), 3-methyl-1-propin-3-yl-thio, 2-butin-4-yl-thio, cyclopropylthio, cyanocyclopropylthio, carboxycyclopropylthio, difluorocyclopropylthio, dichlorocyclopropylthio, methylcyclopropylthio, methoxycarbonylcyclopropylthio, ethoxycarbonylcyclopropylthio, cyclobutylthio, cyanocyclobutylthio, carboxycyclobutylthio, difluorocyclobutylthio, trifluorocyclobutylthio, tetrafluorocyclobutylthio, chlorotrifluorocyclobutylthio, methylcyclobutylthio, cyclopentylthio, cyanocyclopentylthio, carboxycyclopentylthio, fluorocyclopentylthio, chlorocyclopentylthio, difluorocyclopentylthio, dichlorocyclopentylthio, methylcyclopentylthio, methoxycarbonylcyclopentylthio, ethoxycarbonylcyclopentylthio, cyclohexylthio, cyanocyclohexylthio, carboxycyclohexylthio, fluorocyclohexylthio, chlorocyclohexylthio, difluorocyclohexylthio, dichlorocyclohexylthio, methylcyclohexylthio, trifluoromethylcyclohexylthio, methoxycarbonylcyclohexylthio, ethoxycarbonylcyclohexylthio, cyclopropylmethylthio, difluorocyclopropylmethylthio, dichlorocyclopropylmethylthio, cyclobutylmethylthio, cyclopentylmethylthio, cyclohexylmethylthio, cyanocyclohexylmethylthio, carboxycyclohexylmethylthio, fluorocyclohexylmethylthio, chlorocyclohexylmethylthio, methylcyclohexylmethylthio, methylamino, ethylamino, n- or i-propylamino, n-, i-, s- or t-butylamino, n-, i-, s- or t-pentylamino, cyanomethylamino, cyanoethylamino, cyanopropylamino, cyanobutylamino, carboxymethylamino, carboxyethylamino, carboxypropylamino, carboxybutylamino, methoxymethylamino, ethoxymethylamino, propoxymethylamino, methoxyethylamino, ethoxyethylamino, propoxyethylamino, methoxypropylamino, ethoxypropylamino, propoxypropylamino, methoxycarbonylmethylamino, ethoxycarbonylmethyamino, propoxycarbonylmethylamino, methoxycarbonylethylamino, ethoxycarbonylethylamino, propoxycarbonylethylamino, methoxycarbonylpropyamino, ethoxycarbonylpropyamino, propoxycarbonylpropylamino, 1-propen-3-yl-amino (allylamino), 3-methyl-1-propen-3-ylamino, -2-buten-4-yl-amino(crotonylamino), 1-propin-3-yl-amino (propargylamino), 3-methyl-1-propin-3-yl-amino, 2-butin-4-yl-amino, cyclopropylamino, cyanocyclopropylamino, carboxycyclopropylamino, difluorocyclopropylamino, dichlorolcyclopropylamino, methylcycopropylamino, methoxycarbonylcyclopropylamino, ethoxycarbonylcyclopropylamino, cyclobutylamino, cyanocyclobutylamino, carboxycyclobutylamino, difluorocyclobutylamino, trifluorocyclobutylamino, tetrafluorocyclobutylamino, chlorotrifluorocyclobutylamino, methylcyclobutylamino, cyclopentylamino, cyanocyclopentylamino, carboxycyclopentylamino, fluorocyclopentylamino, chlorocyclopentylamino, difluorocyclopentylamino, dichlorocyclopentylamino, methylcyclopentylamino, methoxycarbonylcyclopentylamino, ethoxycarbonylcyclopentylamino, cyclohexylamino, cyanocyclohexylamino, carboxycyclohexylamino, fluorocyclohexylamino, chlorocyclohexylamino, difluorocyclohexylamino, dichlorocyclohexylamino, methylcyclohexylamino, trifluoromethylcyclohexylamino, methoxycarbonylcyclohexylamino, ethoxycarbonylcyclohexylamino, cyclopropylmethylamino, difluorocyclopropylmethylamino, dichlorocyclopropylmethylamino, cyclobutylmethylamino, cyclopentylmethylamino, cyclohexylmethylamino, cyanocyclohexylmethylamino, carboxycyclohexylmethylamino, fluorocyclohexylmethylamino, chlorocyclohexylmethylamino, methylcyclohexylmethylamino, trifluoromethylcyclohexylmethylamino, phenyl, cyanophenyl, carboxyphenyl, nitrophenyl, fluorophenyl, chlorophenyl, bromophenyl, methylphenyl, trifluoromethylphenyl, methoxyphenyl, difluoromethoxyphenyl, trifluoromethoxyphenyl, methoxycarbonylphenyl, ethoxycarbonylphenyl, benzyl, cyanobenzyl, carboxybenzyl, fluorobenzyl, chlorobenzyl, methylbenzyl, trifluoromethylbenzyl, methoxybenzyl, difluoromethoxybenzyl, trifluoromethoxybenzyl, methoxycarbonylbenzyl, ethoxycarbonylbenzyl, phenylethyl, furyl, furylmethyl, tetrahydrofuryl, tetrahydrofurylmethyl, thienyl, tetrahydrothienyl, oxetanyl, oxazolyl, isoxazolyl, phenoxy, cyanophenoxy, carboxyphenoxy, nitrophenoxy, fluorophenoxy, chlorophenoxy, bromophenoxy, methylphenoxy, trifluoromethylphenoxy, methoxyphenoxy, difluoromethoxyphenoxy, trifluoromethoxyphenoxy, methoxycarbonylphenoxy, ethoxycarbonylphenoxy, benzyloxy, cyanobenzyloxy, carboxybenzyloxy, fluorobenzyloxy, chlorobenzyloxy, methylbenzyloxy, trifluoromethylbenzyloxy, methoxybenzyloxy, difluoromethoxybenzyloxy, trifluoromethoxybenzyloxy, methoxycarbonylbenzyloxy, ethoxycarbonylbenzyloxy, phenylethoxy, furyloxy, furylmethoxy, tetrahydrofuryloxy, tetrahydrofurylmethoxy, thienyloxy, tetrahydrothienyloxy, oxetanyloxy, oxazolyloxy, isoxazolyloxy, phenylthio, cyanophenylthio, carboxyphenylthio, nitrophenylthio, fluorophenylthio, chlorophenylthio, bromophenylthio, methylphenylthio, trifluoromethylphenylthio, methoxyphenylthio, difluoromethoxyphenylthio, trifluoromethoxyphenylthio, methoxycarbonylphenylthio, ethoxycarbonylphenylthio, benzylthio, cyanobenzylthio, carboxybenzylthio, fluorobenzylthio, chlorobenzylthio, methylbenzylthio, trifluoromethylbenzylthio, methoxybenzylthio, difluoromethoxybenzylthio, trifluoromethoxybenzylthio, methoxycarbonylbenzylthio, ethoxycarbonylbenzylthio, phenylethylthio, phenylamino, cyanophenylamino, carboxyphenylamino, nitrophenylamino, fluorophenylamino, chlorophenylamino, bromophenylamino, methylphenylamino, trifluoromethylphenylamino, methoxyphenylamino, difluoromethoxyphenyl amino, trifluoromethoxyphenylamino, methoxycarbonylphenylamino,amino,amino, cyanobenzylamino, carboxybenzylamino, fluorobenzylamino, chlorobenzylamino, methylbenzylamino, trifluoromethylbenzylamino, methoxybenzylamino, difluoromethoxybenzylamino, trifluoromethoxybenzylamino, methoxycarbonylbenzylamino, ethoxycarbonylbenzylamino, phenylethylamino, methylsulphonylamino, ethylsulphonylamino, n- or i-propylsulphonylamino, n-, i-, s- or t-butylsulphonylamino, N,N-(bis-methylsulphonyl)-amino, N,N-(bis-ethylsulphonyl)-amino, N-methylsulphonyl -N-ethylsulphonyl-amino, N-methylsulphonyl-N-propylsulphonyl-amino, N-acetyl-N -methylsulphonylamino, N-acetyl-N-ethylsulphonylamino, N-propionyl-N-methylsulphonyl-amino, N-propionyl-N-ethylsulphonyl-amino, N-n-butyroyl-N-methylsulphonyl-amino, N-n-butyroyl-N-ethylsulphonyl-amino, N-i-butyroyl-N-methylsulphonyl-amino, N-i-butyroyl-N-ethylsulphonyl-amino, N-n-valeroyl-N-methylsulphonyl-amino, N-n-valeroyl-N-ethylsulphonyl-amino, N-i-valeroyl-N-methylsulphonyl-amino, N-i-valeroyl-N-ethylsulphonyl-amino, N-s-valeroyl-N-methylsulphonyl-amino, N-s-valeroyl-N-ethylsulphonyl-amino, N-t-butyl-carbonyl-N-methylsulphonyl-amino, N-t-butyl-carbonyl-N-ethylsulphonyl-amino, N-benzoyl-N-methylsulphonyl-amino, N-benzoyl-N-ethylsulphonyl-amino.

Group 2

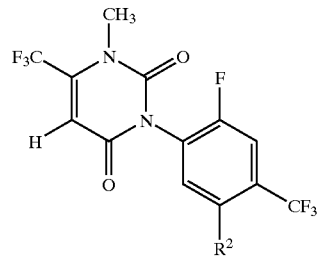

$R^2$ has, for example, the meanings given above in Group 1.

Group 3

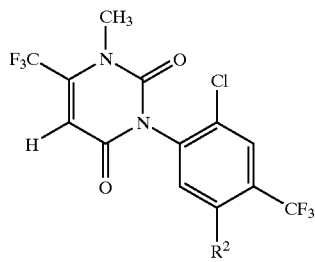

R² has, for example, the meanings given above in Group 1.

Group 4

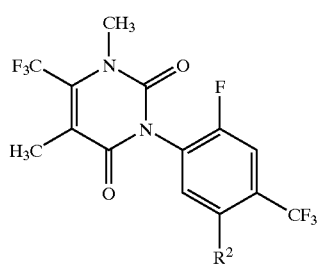

R² has, for example, the meanings given above in Group 1.

Group 5

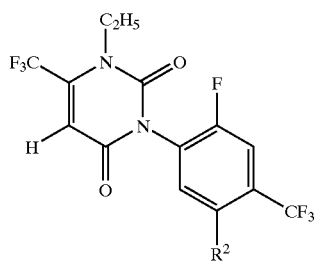

R² has, for example, the meanings given above in Group 1.

Group 6

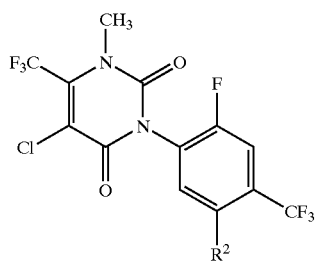

R² has, for example, the meanings given above in Group 1.

Group 7

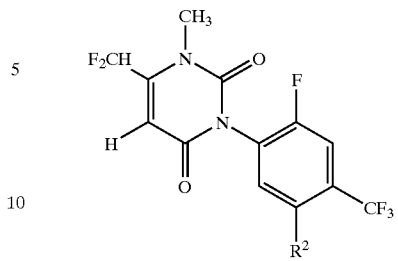

R² has, for example, the meanings given above in Group 1.

Group 8

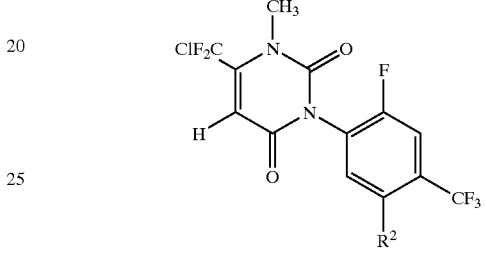

R² has, for example, the meanings given above in Group 1.

Group 9

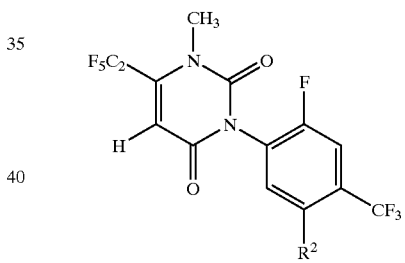

R² has, for example, the meanings given above in Group 1.

Group 10

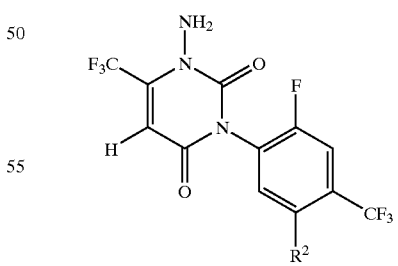

R² has, for example, the meanings given above in Group 1.

Using, for example, methyl 3-amino-crotonate and 2,5-difluoro-4-trifluoromethyl-phenyl isocyanate as starting materials, the course of the reaction in the process according to the invention can thus be illustrated by the following scheme:

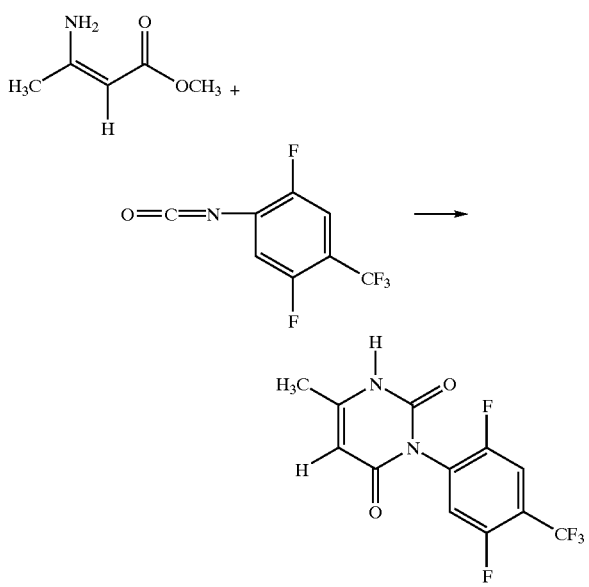

The formula (II) provides a general definition of the aminoalkenoic esters to be used as starting materials in the process according to the invention for preparing compounds of the formula (I). In the formula (II), $R^3$ and $R^4$ preferably or in particular have those meanings which have already been indicated above, in connection with the description of compounds of the formula (I)-according to the invention, as being preferred or as being particularly preferred for $R^3$ and $R^4$.

The starting materials of the formula (II) are known and/or can be prepared by known processes (cf. J. Heterocycl. Chem. 9 (1972), 513–522).

The formula (III) provides a general definition of the p-trifluoromethylphenyl isocyanates further to be used as starting materials in the process according to the invention for preparing compounds of the formula (1). In the formula (111), $R^1$ and $R^2$ preferably or in particular have those meanings which have already been indicated above, in connection with the description of the compounds of the formula (I) according to the invention, as being preferred or as being particularly preferred for $R^1$ and $R^2$.

The starting materials of the formula (III) are known and/or can be prepared by known processes (cf. EP 246061).

The p-trifluoromethylphenyl isocyanates of the general formula (III) are obtained when p-trifluoromethylanilines of the general formula (V)

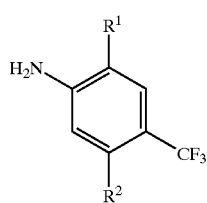

(V)

in which
$R^1$ and $R^2$ are each as defined above
are reacted with phosgene in the presence of a diluent, such as, for example, chlorobenzene, at temperatures between −20° C. and +150° C. (cf. also, for example, EP 648749).

The formula (IV) provides a general definition of the p-trifluoromethylphenylurethanes optionally to be used as starting materials in the process according to the invention. In the formula (IV), $R^1$ and $R^2$ preferably or in particular have those meanings which have already been indicated above, in connection with the description of the compounds of the formula (I) according to the invention, as being preferred or as being particularly preferred for $R^1$ and $R^2$; R preferably represents $C_1$–$C_4$-alkyl, phenyl or benzyl, in particular methyl or phenyl.

The starting materials of the formula (IV) have hitherto not been disclosed in the literature; as novel compounds, they also form part of the subject-matter of the present application.

The novel p-trifluoromethylphenylurethanes of the general formula (IV) are obtained when p-trifluoromethylanilines of the general formula (V)

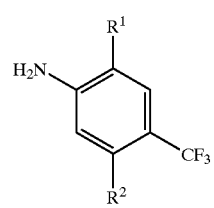

(V)

in which
$R^1$ and $R^2$ are each as defined above
are reacted with chlorocarbonyl compounds of the general formula (VI)

RO—CO—Cl  (VI)

in which
R is as defined above,
if appropriate in the presence of an acid acceptor, such as, for example, pyridine, and
if appropriate in the presence of a diluent, such as, for example, methylene chloride, at temperatures between −20° C. and +100° C. (cf. the preparation examples).

Suitable reaction auxiliaries for the process according to the invention for preparing the compounds of the formula (I) are generally the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds, such as, for example, trimethylamine, triethylamine, tripropylamine, tributylamine, ethyl-diisopropylamine, N,N-dimethylcyclohexylamine, dicyclohexylamine, ethyl -dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methylpyridine, 4-dimethylamino-pyridine, N-methyl -piperidine, 1,4-diazabicyclo[2,2,2]-octane (DABCO), 1,5-diazabicyclo[4,3,0]-non-5-ene (DBN) or 1,8 diazabicyclo[5,4,0]-undec-7-ene (DBU).

Suitable diluents for carrying out the process according to the invention are in particular inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N -dimethylformamide, N,N-dimethylacetamide, N-methylformanilide, N-methylpyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the process according to the invention, the reaction temperatures can be varied within a relatively wide range. In general, the reaction is carried out at temperatures between 0° C. and 200° C., preferably between 10° C. and 150° C.

The process according to the invention is generally carried out under atmospheric pressure. However, it is also possible to carry out the process according to the invention under elevated or reduced pressure—generally between 0.1 bar and 10 bar.

For carrying out the process according to the invention, the starting materials are generally employed in approximately equimolar amounts. However, it is also possible to use one of the components in a relatively large excess. The reaction is generally carried out in a suitable solvent in the presence of a reaction auxiliary, and the reaction mixture is generally stirred for a number of hours at the required temperature. Work-up is carried out by customary methods (cf. the preparation examples).

The active compounds according to the invention can be used as defoliants, desiccants, haulm killers and, especially, as weedkillers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:
Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus and Taraxacum
Dicotyledonous cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.
Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.
Monocotyledonous cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and open spaces with or without tree plantings. Equally, the compounds can be employed for the control of weeds in perennial crops for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture land, and for the selective control of weeds in annual crops.

The compounds of the formula (I) according to the invention are particularly suitable for the selective control of monocotyledonous and dicotyledonous weeds in monocotyledonous and dicotyledonous crops, both pre-emergence and postemergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifying agents and/or dispersing agents and/or foam-forming agents.

If the extender used is water, it is also possible to employ for example organic solvents as auxiliary solvents. Suitable liquid solvents are essentially the following: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates;. suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For the control of weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlomitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop(-ethyl), flamprop(-iso-propyl), flamprop(-isopropyl-L), flamprop(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-iso-propylammonium), halosafen, haloxyfop (-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metsulfuron(methyl), metribuzin, molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium), quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a relatively wide range. It depends essentially on the nature of the desired effect. In general, the amounts used are between 1 g and. 10 kg of active compound per hectare of soil surface, preferably between 5 g and 5 kg per ha.

The preparation and use of the active compounds according to the invention can be seen from the following examples.

PREPARATION EXAMPLES

Example 1

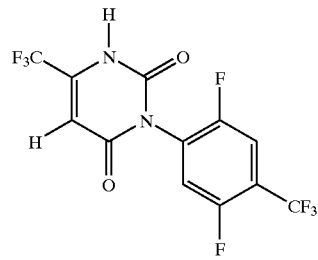

At room temperature (approximately 25° C.), a mixture of 24.4 g (0.97 mol) of ethyl 3-amino-4,4,4-trifluoro-crotonate, 3.75 g of sodium hydride and 80 ml of N,N-dimethyl-formamide is stirred for about 30 minutes. After addition of 26 g (0.97 mol) of N-(2,5-difluoro4-trifluoromethyl-phenyl)-O-ethyl-urethane, the reaction mixture is stirred at 125° C. to 130° C. for about 2 hours, cooled slightly, put onto ice-water, acidified with hydrochloric acid and shaken with ethyl acetate. The organic phase is separated off, washed with water, dried with sodium sulphate and filtered. The filtrate is concentrated under water pump vacuum, the residue is digested with a mixture of 5 ml of ethyl acetate, 10 ml of diethyl ether and 300 ml of petroleum ether and the crystalline product is isolated by filtration with suction.

This gives 19.1 g (55% of theory) of 1-(2,5-difluoro4-trifluoromethyl-phenyl)-3,6-dihydro-2,6-dioxo-4-trifluoromethyl-1(2H)-pyrimidine of melting point 217° C.

Example 2

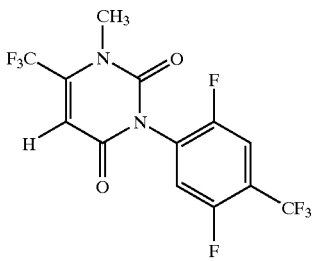

A mixture of 1.8 g (5 mmol) of 1-(2,5-difluoro-4-trifluoromethyl-phenyl)-3,6-dihydro-2,6-dioxo-4-trifluoromethyl-1(2H)-pyrimidine, 0.75 g (5 mmol) of dimethyl sulphate, 0.83 g of potassium carbonate and 30 ml of acetone is heated under reflux for approximately 45 minutes and then concentrated under water pump vacuum. The residue is stirred with 50 ml of water/50 ml of petroleum ether and the crystalline product is isolated by filtration with suction.

This gives 1.4 g (75% of theory) of 1-(2,5-difluoro-4-trifluoromethyl-phenyl)-3,6-dihydro-2,6-dioxo-3-methyl-4-trifluoromethyl-1 (2H)-pyrimidine of melting point 110° C.

Example 3

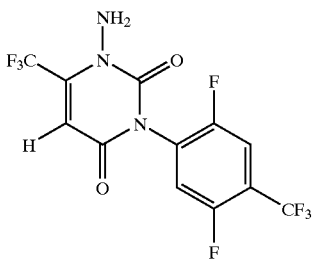

At room temperature (approximately 20° C.), a mixture of 2.52 g (7 mmol) of 1-(2,5-difluoro-4-trifluoromethyl-phenyl)-3,6-dihydro-2,6-dioxo-4-trifluoromethyl-1 (2H)-pyrimidine, 1.6 g (7 mmol) of 1-aminooxy-2,4-dinitro-benzene, 0.75 g of sodium bicarbonate and 20 ml of N,N-dimethyl-formamide is stirred for 8 days. The mixture is then shaken with 5% strength aqueous sodium hydroxide solution/diethyl ether. The organic phase is washed with 5% strength aqueous sodium hydroxide solution and then with water, dried with sodium sulphate and filtered. The filtrate is concentrated under water pump vacuum, the residue is digested with 5 ml of diethyl ether/10 ml of petroleum ether and the crystalline product is isolated by filtration with suction.

This gives 0.95 g (36% of theory) of 3-amino-1-(2,5-difluoro-4-trifluoromethyl-phenyl)-3,6-dihydro-2,6-dioxo-4-trifluoromethyl-1 (2H)-pyrimidine of melting point 157° C.

Example 4

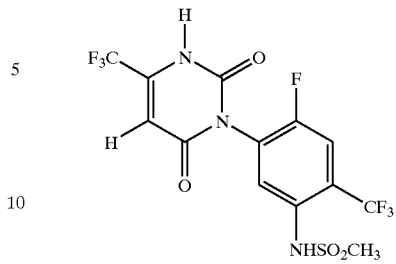

At 170° C., a mixture of 10 g (27.8 mmol) of 1-(2,5-difluoro-4-trifluoromethyl-phenyl)-3,6-dihydro-2,6-dioxo-4-trifluoromethyl-1 (2H)-pyrimidine, 5.8 g (27.8 mmol) of methanesulphonamide, 12 g of potassium carbonate and 40 ml of N-methyl-pyrrolidone is stirred for approximately 35 hours. After cooling to room temperature, the mixture is poured onto ice-water, acidified with 2N hydrochloric acid and extracted with ethyl acetate. The organic phase is washed with water, dried with sodium sulphate and filtered. The filtrate is concentrated under water pump vacuum, the residue is digested with 0.5 ml of ethyl acetate/3 ml of diethyl ether and the crystalline product is isolated by filtration with suction.

This gives 3.6 g (30% of theory) (27.8 mmol) of 1-(2-fluoro-5-methylsulphonyl-4-trifluoromethyl-phenyl)-3,6-dihydro-2,6-dioxo-4-trifluoromethyl-1 (2H)-pyrimidine of melting point 227° C.

Example 5

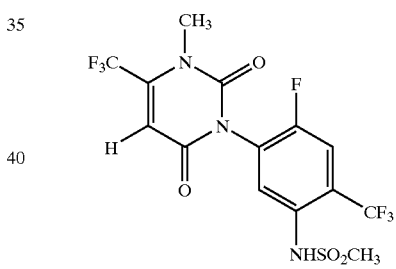

A mixture of 1.0 g (2.3 mmol) of 1-(2-fluoro-5-methylsulphonyl-5-trifluoromethyl-phenyl)-3,6-dihydro-2,6-dioxo4-trifluoromethyl-1(2H)-pyrimidine, 0.31 g (2.3 mmol) of dimethyl sulphate, 0.21 g of sodium bicarbonate and 20 ml of acetone is heated under reflux for 7 hours and subsequently concentrated under water pump vacuum. The residue is shaken with diethyl ether and 2N hydrochloric acid and the organic phase is separated off, washed with water, dried with sodium sulphate and filtered. The filtrate is concentrated under water pump vacuum, the residue is digested with diethyl ether and the crystalline product is isolated by filtration with suction.

This gives 0.62 g (60% of theory) of 1-(2-fluoro-5-methylsulphonyl-4-trifluoromethyl-phenyl)-3,6-dihydro-2,6-dioxo-3-methyl-4-trifluoromethyl-1(2H)-pyrimidine of melting point 163° C.

Similarly to the Preparation Examples 1 to 5, and in accordance with the general description of the preparation process according to the invention, it is also possible to prepare, for example, the compounds of the formula (1) listed in Table 1 below.

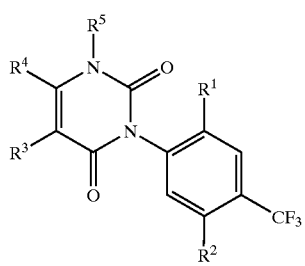

(I)

TABLE 1

Examples of compounds of the formula (I)

| Ex. No. | R¹ | R² | R³ | R⁴ | R⁵ | Melting point (° C.) |
|---|---|---|---|---|---|---|
| 6 | F | $N(SO_2CH_3)_2$ | H | $CF_3$ | H | 246 |
| 7 | F | $N(SO_2CH_3)_2$ | H | $CF_3$ | $NH_2$ | 270 |
| 8 | F | $NHSO_2CH_3$ | H | $CF_3$ | $NH_2$ | 156 |
| 9 | F | N(CH₃)(SO₂)–C(=O)–thiophen-2-yl | H | $CF_3$ | $NH_2$ | 246 |
| 10 | F | $NHSO_2C_2H_5$ | H | $CF_3$ | H | 175 |
| 11 | F | $NHSO_2C_2H_5$ | H | $CF_3$ | $CH_3$ | |
| 12 | F | N(C₂H₅)(SO₂)–C(=O)–OC₂H₅ | H | $CF_3$ | H | 135 |
| 13 | F | N(C₂H₅)(SO₂)–C(=O)–OC₂H₅ | H | $CF_3$ | $CH_3$ | (amorphous) |
| 14 | F | N(CH₃)(SO₂)–C(=O)–C(CH₃)₃ | H | $CF_3$ | $CH_3$ | 217 |
| 15 | F | N(CH₃)(SO₂)–C(=O)–phenyl | H | $CF_3$ | $CH_3$ | 180 |
| 16 | F | N(CH₃)(SO₂)–C(=O)–(4-Cl-phenyl) | H | $CF_3$ | $CH_3$ | 196 |
| 17 | F | N(CH₃)(SO₂)–C(=O)–(4-OCH₃-phenyl) | H | $CF_3$ | $CH_3$ | 209 |
| 18 | F | N(C₂H₅)(SO₂)–C(=O)–C(CH₃)₃ | H | $CF_3$ | $CH_3$ | |
| 19 | F | N(C₂H₅)(SO₂)–C(=O)–phenyl | H | $CF_3$ | $CH_3$ | |
| 20 | F | N(C₂H₅)(SO₂)–C(=O)–(4-OCH₃-phenyl) | H | $CF_3$ | $CH_3$ | |
| 21 | F | N(C₂H₅)(SO₂)–C(=O)–thiophen-2-yl | H | $CF_3$ | $CH_3$ | |
| 22 | F | $—NHSO_2C_2H_5$ | H | $CF_3$ | $NH_2$ | |
| 23 | F | $—N(SO_2C_2H_5)_2$ | H | $CF_3$ | $NH_2$ | |
| 24 | F | $—N(SO_2C_2H_5)_2$ | H | $CF_3$ | $CH_3$ | |

TABLE 1-continued

Examples of compounds of the formula (I)

| Ex. No. | R¹ | R² | R³ | R⁴ | R⁵ | Melting point (° C.) |
|---|---|---|---|---|---|---|
| 25 | F | -N(SO₂C₂H₅)-CO-C(CH₃)₃ | H | CF₃ | NH₂ | |
| 26 | F | -N(SO₂C₂H₅)-CO-phenyl | H | CF₃ | NH₂ | |
| 27 | F | -N(SO₂C₂H₅)-CO-(4-OCH₃-phenyl) | H | CF₃ | NH₂ | |
| 28 | F | -N(SO₂C₂H₅)-CO-(2-thienyl) | H | CF₃ | NH₂ | |
| 29 | F | —CO-tC₄H₉ | H | CF₃ | CH₃ | |
| 30 | F | —CO-phenyl | H | CF₃ | CH₃ | |
| 31 | F | —CO-(4-OCH₃-phenyl) | H | CF₃ | CH₃ | |
| 32 | F | —CO-(2-thienyl) | H | CF₃ | CH₃ | |
| 33 | F | H | H | CF₃ | NH₂ | |
| 34 | F | SO₂C₂H₅ | H | CF₃ | NH₂ | |
| 35 | F | SO₂C₂H₅ | H | CF₃ | CH₃ | |
| 36 | F | —CO-tC₄H₉ | H | CF₃ | NH₂ | |
| 37 | F | —CO-phenyl | H | CF₃ | NH₂ | |
| 38 | F | —CO-(4-OCH₃-phenyl) | H | CF₃ | NH₂ | |
| 39 | F | —CO-(2-thienyl) | H | CF₃ | NH₂ | |

Starting Materials of the Formula (IV):

Example (IV-1)

[Structure: C₂H₅-O-C(=O)-NH-(2,5-difluoro-4-CF₃-phenyl)]

With stirring, 11.7 g (104 mmol) of ethyl chloroformate are added to a mixture of 20.5 g (104 mmol) of 2,5-difluoro-4-trifluoromethyl-aniline, 8.5 g of pyridine and 200 ml of dichloromethane which had been cooled to 0° C. The reaction mixture is stirred at 0° C. for 60 minutes and then washed with 2N hydrochloric acid and with water, dried with sodium sulphate and filtered. The filtrate is concentrated under water pump vacuum, the residue is digested with petroleum ether and the crystalline product is isolated by filtration with suction.

This gives 26.2 g (93.5% of theory) of N-(2,5-difluoro-4-trifluoromethyl-phenyl)-O-ethyl-urethane of melting point 92° C.

USE EXAMPLES

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound in such a way as to apply the particular amounts of active compound desired per unit area. The concentration of the spray liquor is chosen so that the particular amounts of active compound desired are applied in 1000 l of water/ha.

After 3 weeks, the degree of damage to plants is rated in % damage in comparison to the development of the untreated control.

The figures denote:

0%=no effect (like untreated control)

100%=total destruction

In this test, the compounds of Preparation Examples 2, 4 and 5, for example, show strong activity against weeds, such as Cyperus (80%), Sinapis (100%), Abutilon (80–100%), Chenopodium (80–100%), Matricaria (90–100%) and Solanum (90–100%), and some of them are tolerated well by crop plants, such as, for example, maize (0–10%), wheat (0%), soya (0%) and sugar beet (0%).

Example B

Postemergence Test

Solvent: 5 parts by weight of acetone

Emulsifier: 1 part by weight of alkylaryl polyglycol ether

To produce an effective preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. The concentration of the spray liquor is chosen so that the particular amounts of active compound desired are applied in 1000 l of water/ha.

After 3 weeks, the degree of damage to the plants is rated in % damage in comparison to the development of the untreated control.

The figures denote:

0%=no effect (like untreated control)

100%=total destruction

In this test, the compounds of preparation examples 2, 4 and 5, for example, show strong activity against weeds, such as Sinapis (100%), datura (100%), Ipomoea (100%), polygonum (95%), Solanum (100%), Abutilon (100%) and Matricaria (100%), and some of them are well tolerated by crop plants, such as, for example, maize (0%), wheat (0–5%) and barley (0–10%).

What is claimed is:

1. A substituted p-trifluoromethylphenyluracil of the formula (I)

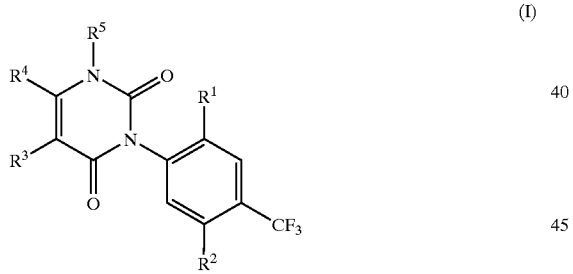

(I)

wherein $R^1$ represents hydrogen, cyano, fluorine, chlorine or bromine, $R^2$ represents a grouping $A^1$—$A^2$—$A^3$ wherein $A^1$ represents a single bond, O, S, —SO—, or $A^1$ represents $C_1$–$C_6$-alkanediyl, $C_2$–$C_6$-alkenediyl, $C_2$–$C_6$-alkynediyl, $C_3$–$C_6$-cycloalkanediyl, $C_3$–$C_6$-cycloalkenediyl or phenylene, each of which is optionally substituted by fluorine or chlorine, $A^2$ represents a single bond, represents O, S, —SO—, —$SO_2$—, —CO— or the grouping

in which $A^4$ represents hydrogen, hydroxyl, $C_1$–$C_4$-alkyl, $C_1$–$C_4$-alkoxy, phenyl, $C_1$–$C_4$-alkylsulphonyl or phenylsulphonyl, or $A^2$ represents $C_1$–$C_6$-alkanediyl, $C_2$–$C_6$-alkenediyl, $C_2$–$C_6$-alkynediyl, $C_3$–$C_6$-cycloalkanediyl, $C_3$–$C_6$-cycloalkenediyl or phenylene, each of which is unsubstituted or substituted by fluorine or chlorine, $A^3$ represents hydrogen, hydroxyl, mercapto, amino, cyano, isocyanato, thiocyanato, nitro, carboxyl, carbamoyl, thiocarbamoyl, sulpho, chlorosulphonyl, halogen;

represents alkyl, alkoxy, alkylthio, alkylsulphinyl, alkylsulphonyl, alkylamino, dialkylamino, alkoxycarbonyl or dialkoxy(thio)phosphoryl having in each case 1 to 6 carbon atoms in the alkyl groups and being in each case unsubstituted or substituted by fluorine, chlorine, bromine or $C_1$–$C_4$-alkoxy;

represents alkenyl, alkenyloxy, alkenylamino, alkylideneamino, alkenyloxycarbonyl, alkynyl, alkynyloxy, alkynylamino or alkynyloxycarbonyl having in each case 2 to 6 carbon atoms in the alkenyl, alkylidene or alkynyl groups and being in each case unsubstituted or substituted by fluorine, chlorine or bromine;

represents cycloalkyl, cycloalkyloxy, cycloalkylalkyl, cycloalkylalkoxy, cycloalkylideneamino, cycloalkyloxycarbonyl or cycloalkylalkoxycarbonyl having in each case 3 to 6 carbon atoms in the cycloalkyl groups and 0 to 4 carbon atoms in the alkyl groups and being in each case unsubstituted or substituted by a moiety selected from the group consisting of fluorine, chlorine, bromine, cyano, carboxyl, $C_1$–$C_4$-alkyl and $C_1$–$C_4$-alkoxy-carbonyl; represents phenyl, phenyloxy, phenyl-$C_1$–$C_4$-alkyl, phenyl-$C_1$–$C_4$-alkoxy, phenyloxycarbonyl or phenyl-$C_1$–$C_4$-alkoxy-carbonyl, each of which is unsubstituted or substituted by a moiety selected from the group consisting of nitro, cyano, carboxyl, fluorine, chlorine, bromine, $C_1$–$C_4$-alkyl, $C_1$–$C_4$-halogenoalkyl, $C_1$–$C_4$-alkyloxy, $C_1$–$C_4$-halogenoalkyloxy and $C_1$–$C_4$-alkoxycarbonyl; or represents in each case unhydrogenated or fully or partially hydrogenated pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazol-$C_1$–$C_4$-alkyl, thiazole-$C_1$–$C_4$-alkyl, pyridinyl-$C_1$–$C_4$-alkyl, pyrimidinyl-$C_1$–$C_4$-alkyl, pyrazolylmethoxy, furylmethoxy, perhydropyranylmethoxy or pyridylmethoxy, $R^3$ represents hydrogen, fluorine, chlorine, bromine or unsubstituted or fluorine or chlorine-substituted or fluorine- and chlorine-substituted alkyl having 1 to 4 carbon atoms, $R^4$ represents unsubstituted or fluorine- or chlorine-substituted or fluorine- and chlorine-substituted alkyl having 1 to 4 carbon atoms, and $R^5$ represents amino.

2. A substituted p-trifluoromethylphenyluracil of the formula (I) according to claim 1, wherein $R^1$ represents hydrogen, fluorine or chlorine, $R^2$ represents a grouping $A^1$—$A^2$—$A^3$ wherein $A^1$ represents a single bond, O, S, —SO—, or $A^1$ represents methylene, ethane-1,1-diyl, ethane-1,2-diyl, propane-1,1-diyl, propane-1,2-diyl, propane-1, 3-diyl, ethene-1,2-diyl, propene-1,2-diyl, propene-1,3-diyl, ethine-1,2-diyl or propine-1,3-diyl, $A^2$ represents a single bond, O, S, —SO—, —SO$_2$—, —CO— or the grouping

in which $A^4$ represents hydrogen, hydroxyl, methyl, ethyl, n- or i-propyl, methylsulphonyl, ethylsulphonyl, n- or i-propylsulphonyl or phenylsulphonyl, or $A^2$ represents methyl, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl or propine-1,3-diyl, $A^3$ represents hydrogen, hydroxyl, amino, cyano, nitro, carboxyl, carbamoyl, sulpho, fluorine, chlorine, bromine, represents methyl, ethyl, n- or i-propyl, n-, i-, s- or t-butyl, n-, i-, s- or t-pentyl, methoxy, ethoxy, n- or i-propoxy, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl, dipropoxyphosphoryl dimethoxyphosphoryl, diethoxyphosphoryl, dipropoxyphosphoryl or diisopropoxyphosphoryl, each of which is unsubstituted or substituted by fluorine, chlorine, methoxy or ethoxy;

represents propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, each of which is unsubstituted or substituted by fluorine or chlorine;

represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopentylideneamino, cyclohexylideneamino, cyclopentyloxycarbonyl, cyclohexyloxycarbonyl, cyclopentylmethoxycarbonyl or cyclohexylmethoxycarbonyl, each of which is unsubstituted or substituted by fluorine, chlorine, cyano, carboxyl, methyl, ethyl, n- or i-propyl, methoxycarbonyl or ethoxycarbonyl;

represents phenyl, phenyloxy, benzyl, phenylethyl, benzyloxy, phenyloxycarbonyl, benzyloxycarbonyl, each of which is unsubstituted or substituted by a moiety selected from the group consisting of nitro, cyano, carboxyl, fluorine, chlorine, bromine, methyl, ethyl, n- or i-propyl, trifluoromethyl, methoxy, ethoxy, n- or i-propoxy, difluoromethoxy, trifluoromethoxy, methoxycarbonyl and ethoxycarbonyl, or represents in each case unhydrogenated or fully or partially hydrogenated pyrrolyl, pyrazolyl, imidazolyl, triazolyl, furyl, thienyl, oxazolyl, isoxazolyl, thiazolyl, isothiazolyl, oxadiazolyl, thioadiazolyl, pyridinyl, pyrimidinyl, triazinyl, pyrazolylmethyl, furylmethyl, thienylmethyl, oxazolylmethyl, isoxazolmethyl, thiazolemethyl, pyridinylmethyl, pyrimidinylmethyl, pyrazolylmethoxy, furylmethoxy or pyridylmethoxy, $R^3$ represents hydrogen, fluorine, chlorine or in each case unsubstituted or fluorine- or chlorine-substituted or fluorine- and chlorine-substituted methyl or ethyl, $R^4$ represents in each case fluorine- or chlorine-substituted or fluorine- and chlorine-substituted methyl or ethyl, and $R^5$ represents amino.

3. A herbicidal composition, comprising at least one p-trifluoromethylphenyluracil of the formula (I) according to claim 1 and at least one extender and/or surfactant.

4. A method for controlling undesirable plants, comprising the step of allowing a herbicidally effective amount of a p-trifluoromethylphenyluracil of the formula (I) according to claim 1 to act on undesirable plants and/or their habitat.

* * * * *